(12) United States Patent
Yang et al.

(10) Patent No.: US 11,389,065 B2
(45) Date of Patent: Jul. 19, 2022

(54) OCT IMAGE PROCESSING DEVICE AND SYSTEM

(71) Applicants: Shenzhen Institute of Terahertz Technology and Innovation, Guangdong (CN); Xiongan China Communication Technology Co., Ltd., Baoding (CN)

(72) Inventors: Minwei Yang, Guangdong (CN); Junqiu Zhan, Guangdong (CN); Qing Ding, Guangdong (CN)

(73) Assignees: SHENZHEN INSTITUTE OF TERAHERTZ TECHNOLOGY AND INNOVATION, Shenzhen (CN); XIONGAN CHINA COMMUNICATION TECHNOLOGY CO., LTD., Baoding (CN)

( * ) Notice: Subject to any disclaimer, the term of this patent is extended or adjusted under 35 U.S.C. 154(b) by 292 days.

(21) Appl. No.: 16/728,250

(22) Filed: Dec. 27, 2019

(65) Prior Publication Data

US 2020/0205666 A1 Jul. 2, 2020

(30) Foreign Application Priority Data

Dec. 29, 2018 (CN) .......................... 201811647726.9

(51) Int. Cl.
*A61B 5/00* (2006.01)
*G06T 7/00* (2017.01)
*G01B 9/02091* (2022.01)

(52) U.S. Cl.
CPC .......... *A61B 5/0066* (2013.01); *G06T 7/0012* (2013.01); *G01B 9/02091* (2013.01); *G06T 2207/10101* (2013.01)

(58) Field of Classification Search
CPC ................ A61B 5/0066; G06T 7/0012; G06T 2207/10101; G01B 9/02091
See application file for complete search history.

(56) References Cited

U.S. PATENT DOCUMENTS

| | | | | |
|---|---|---|---|---|
| 2009/0093980 | A1* | 4/2009 | Kemp | A61B 5/0066 702/77 |
| 2014/0181717 | A1* | 6/2014 | Lahti | A61B 5/0035 715/771 |
| 2016/0025478 | A1* | 1/2016 | Johnson | G01B 9/02069 702/191 |

OTHER PUBLICATIONS

Jin et al., "High-Speed FPGA-GPU Processing for 3D-OCT Imaging", 2017 3rd IEEE International Conference on Computer Communications, pp. 2085-2088 (Year: 2017).*

* cited by examiner

*Primary Examiner* — Nay A Maung
*Assistant Examiner* — Jose M Torres
(74) *Attorney, Agent, or Firm* — Panitch Schwarze Belisario & Nadel LLP

(57) ABSTRACT

The invention belongs to the technical field of OCT and provides an OCT image processing device and system. An FPGA is in communication connection with an upper computer via a PCIE interface to receive OCT image data acquired by the upper computer and to carry out image preprocessing on the OCT image data and then send the OCT image data to the upper computer to display. The OCT image data is acquired and displayed by the upper computer and the OCT image data's preprocessing is implemented by the FPGA, so that the processing efficiency of the OCT image data is greatly improved.

9 Claims, 4 Drawing Sheets

OCT IMAGE PROCESSING DEVICE AND SYSTEM

CROSS-REFERENCE TO RELATED APPLICATIONS

This application claims priority under 35 U.S.C. § 119(b) to Chinese Application No. 201811647726.9, filed Dec. 29, 2018, the disclosure of which is incorporated by reference herein in its entirety.

TECHNICAL FIELD

The invention relates to the technical field of OCT (optical coherence tomography), and in particular, to an OCT image processing device and system.

BACKGROUND

The OCT technology is a novel imaging technology implemented based on a partially coherent light interference theory. The principle of the OCT technology is that light emitted by a broadband light source is split to irradiate a sample arm and a reference arm, the backward scattered light and the reference light of a sample return to a beam splitter to generate an interference signal, and a depth image of the sample can be reconstructed by detecting the interference signal, so as to realize an analysis of the internal structure of the sample. The OCT technology has been widely applied to the field of biomedical imaging.

At present, original spectral data is generally acquired by a camera and is then transmitted to an upper computer to process and display. The processing speed is low, and the reconstruction efficiency of sample depth images is low.

SUMMARY

In view of this, the invention provides an OCT image processing device and system to solve the problems of low processing speed and low reconstruction efficiency of sample depth images caused by acquisition of original spectroscopic data by a camera and transmission of the original spectroscopic data to an upper computer for processing and displaying in the prior art.

A first aspect of the invention provides an OCT image processing device comprising an FPGA and a PCIE interface, wherein the FPGA comprises a PCIE transceiver module which is in communication connection with an upper computer via the PCIE interface;

The upper computer is configured to acquire OCT image data and send the OCT image data to the PCIE interface; and The FPGA is configured to receive the OCT image data via the PCIE interface, carry out image preprocessing on the OCT image data, and send, via the PCIE interface, the OCT image data subjected to the image preprocessing to the upper computer to display.

In one embodiment, the FPGA comprises an XDMA module, a memory read-write module, a first VDMA module, an AXIS to VIDEO module, an image preprocessing module, a VIDEO to AXIS module, and a second VDMA module, wherein:

The XDMA module is in communication connection with the PCIE interface and the memory read-write module, the memory read-write module is in communication connection with the first VDMA module and the second VDMA module, the first VDMA module is in communication connection with the AXIS to VIDEO module, the AXIS to VIDEO module is in communication connection with the image preprocessing module, the image preprocessing module is in communication connection with the VIDEO to AXIS module, and the VIDEO to AXIS module is in communication connection with the second VDMA module;

The XDMA module is configured to receive the OCT image data sent from the upper computer via the PCIE interface and write the OCT image data into the memory read-write module;

The memory read-write module is configured to cache the OCT image data;

The first VDMA module is configured to read the OCT image data from the memory read-write module and send the OCT image data to the AXIS to VIDEO module;

The AXIS to VIDEO module is configured to convert the timing sequence of the OCT image data into a video timing sequence and send the OCT image data converted into the video timing sequence to the image preprocessing module;

The image preprocessing module is configured to carry out image preprocessing on the OCT image data converted into the video timing sequence and send the OCT image data subjected to the image preprocessing to the VIDEO to AXIS module;

The VIDEO to AXIS module is configured to send the OCT image data subjected to the image preprocessing to the second VDMA module through an AXI4 bus;

The second VDMA module is configured to write the OCT image data subjected to the image preprocessing into the memory read-write module;

The memory read-write module is further configured to cache the OCT image data subjected to the image preprocessing; and The XDMA module is further configured to read the OCT image data subjected to the image preprocessing from the memory read-write module and send, via the PCIE interface, the OCT image data to the upper computer to display.

In one embodiment, the XDMA module is in communication connection with the PCIE interface through a PCIE bus and is in communication connection with the memory read-write module through an AXI4 bus; and The XDMA module is specifically configured to write the OCT image data received via the PCIE interface into the memory read-write module through the AXI4 bus.

In one embodiment, the first VDMA module is in communication connection with the memory read-write module through an AXI4 bus and is in communication connection with the AXIS to VIDEO module through an AXIS bus; and The first VDMA module is specifically configured to read the OCT image data cached in the memory read-write module through the AXI4 bus and send the OCT image data to the AXIS to VIDEO module through the AXIS bus.

In one embodiment, the image preprocessing module is specifically configured to carry out cubic spline interpolation and Fourier transform on the OCT image data converted into the video timing sequence and send the OCT image data to the VIDEO to AXIS module.

In one embodiment, the image preprocessing module is further specifically configured to transform the OCT image data converted into the video timing sequence into a wavenumber domain before carrying out the cubic spline interpolation and the Fourier transform on the OCT image data converted into the video timing sequence.

In one embodiment, the VIDEO to AXIS module is in communication connection with the second VDMA module through an AXIS bus; and The VIDEO to AXIS module is specifically configured to send the OCT image data subjected to the image preprocessing to the second VDMA module through the AXIS bus.

In one embodiment, the second VDMA module is in communication connection with the memory read-write module through an AXI4 bus; and The second VDMA module is specifically configured to write the OCT image data subjected to the image preprocessing into the memory read-write module through the AXI4 bus.

In one embodiment, the upper computer comprises a CPU which is in communication connection with the PCIE interface through a PCIE bus.

A second aspect of the the invention further provides an OCT image processing system comprising:

The OCT image processing device; and

An upper computer in communication connection with the OCT image processing device.

The OCT image processing device according to the embodiments of this invention comprises the FPGA. The FPGA is in communication connection with the upper computer via the PCIE interface to receive the OCT image data acquired by the upper computer, and to send the OCT image data to the upper computer to display after the image preprocessing on the OCT image. Since the OCT image data is acquired and displayed by the upper computer and is subjected to the image preprocessing by the FPGA, the processing efficiency of the OCT image data is greatly improved.

BRIEF DESCRIPTION OF THE DRAWINGS

For the sake of a clearer explanation of the technical solutions of the embodiments of the invention, a brief description to the accompanying drawings required by the embodiments is given below. Obviously, the accompanying drawings in the following description are only used for illustrating certain embodiments of the invention, and those ordinarily skilled in the art can acquire other accompanying drawings according to the following ones without paying creative effort.

DETAILED DESCRIPTION OF EMBODIMENTS

In order to provide a better understanding of the technical solutions of the invention for those skilled in the art, the technical solutions of the embodiments are clearly described below with reference to the accompanying drawings. Obviously, the embodiments in the following description are illustrative ones only, and are not all possible ones of the invention. All other embodiments obtained by those ordinarily skilled in the art based on these illustrative ones without paying creative effort should also fall within the scope of the invention.

The term "comprise" involved in the description, claims and accompanying drawings, and any transformations of this term refer to non-exclusive inclusion. For instance, a process or method comprising a series of steps, or a system, product or device comprising a series of units is not limited to the steps or units listed, and may optionally comprise steps or units not listed, or comprise other intrinsic steps of the process or method or other intrinsic units of the system, product or device. Besides, terms "first", "second", and "third" are used for distinguishing different objects, not for describing a specific sequence.

Embodiment 1

Figure 1:
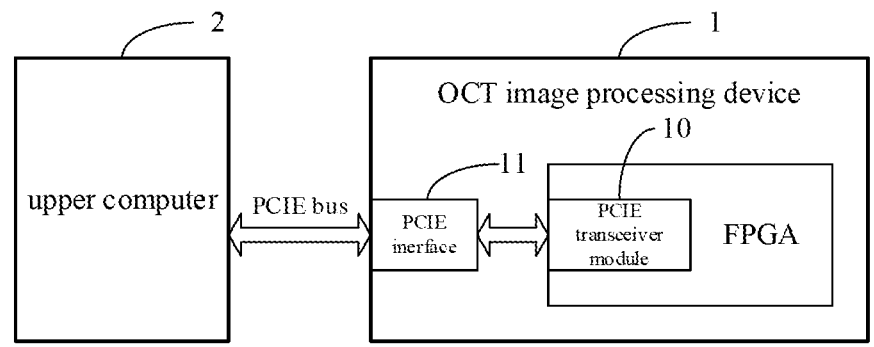
FIG. 1 is a structural view of an OCT image processing device according to Embodiment 1 of the invention.

As shown in FIG. 1, an OCT image processing device 1 comprises an FPGA (Field-Programmable Gate Array) and a PCIE (peripheral component interconnect express) interface 11, wherein the FPGA comprises a PCIE transceiver module 10 which is in communication connection with an upper computer 2 via the PCIE interface.

In a specific application, the upper computer can be any device having data processing and control functions, such as a PC (Personal Computer) client, a notebook computer, a mobile phone, a tablet computer, a server, and an industrial personal computer. The upper computer comprises a display or is in communication connection with the display, and the upper computer is in communication connection with a camera to acquire OCT image data. The OCT image processing device may only comprise a shell and the FPGA.

In this embodiment, the upper computer 2 is configured to acquire the OCT image data and sending the OCT image data to the PCIE interface through a PCIE bus; and The FPGA is configured to receive the OCT image data via the PCIE interface 11, carry out image preprocessing on the OCT image data, and send, via the PCIE interface 11, the OCT image data subjected to the image preprocessing to the upper computer to display.

In a specific application, the image preprocessing specifically comprises cubic spline interpolation and Fourier transformation.

Embodiment 2

Figure 2:
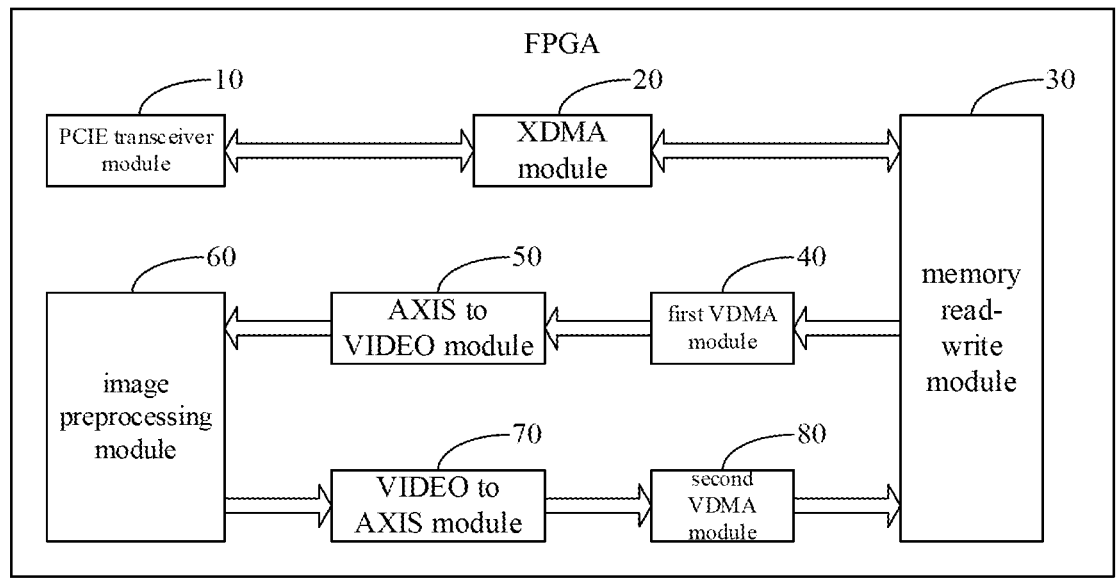
FIG. 2 is a structural view of an FPGA according to Embodiment 2 of the invention.

As shown in FIG. 2, in this embodiment, the FPGA in Embodiment 1 comprises an XDMA module 20, a memory read-write module 30, a first VDMA module 40, an AXIS to VIDEO module 50, an image preprocessing module 60, a VIDEO to AXIS module 70, and a second VDMA module 80.

In a specific application, XDMA is a PCIE DMA transfer IP packaged by Xilinx; the memory read-write module is particularly a DDR SDRAM (Double Data Rate Synchronous Dynamic Random Access Memory) or is used for realizing reading and writing of the DDR SDRAM which is in communication connection with the FPGA; VDMA is also an IP provided by Xilinx, and the VDMA is essentially a core used for realizing data transfer, which is configured to cache multi-frame image data, thus facilitating the data being written into or read out of the memory read-write module. The first VDMA module and the second VDMA module are implemented in the same manner and have identical effect.

In a specific application, the modules in the FPGA are functional regions used for fulfilling corresponding software functions and are respectively implemented by sublogic circuits in the FPGA.

In this embodiment, the XDMA module 20 is in communication connection with the PCIE interface 11 and the memory read-write module 30. The memory read-write module 30 is in communication connection with the first VDMA module 40 and the second VDMA module 80 The first VDMA module 40 is in communication connection with the AXIS to VIDEO module 50 The AXIS to VIDEO module 50 is in communication connection with the image preprocessing module 60 The image preprocessing module 60 is in communication connection with the VIDEO to AXIS module 70, and the VIDEO to AXIS module 70 is in communication connection with the second VDMA module 80.

In this embodiment, the functional modules have the following functions:

The XDMA module 20 is configured to receive the OCT image data sent from the upper computer 2 via the PCIE interface 11 and write the OCT image data into the memory read-write module 30;

The memory read-write module 30 is configured to cache the OCT image data;

The first VDMA module 40 is configured to read the OCT image data from the memory read-write module and send the OCT image data to the AXIS to VIDEO module 50;

The AXIS to VIDEO module 50 is configured to convert the timing sequence of the OCT image data into a video timing sequence and send the OCT image data converted into the video timing sequence to the image preprocessing module 60;

The image preprocessing module 60 is configured to carry out image preprocessing on the OCT image data converted into the video timing sequence and send the OCT image data subjected to the image preprocessing to the VIDEO to AXIS module 70;

The VIDEO to AXIS module 70 is configured to send the OCT image data subjected to the image preprocessing to the second VDMA module 80 through an AXI4 bus;

The second VDMA module 80 is configured to write the OCT image data subjected to the image preprocessing into the memory read-write module 30;

The memory read-write module 30 is further configured to cache the OCT image data subjected to the image preprocessing; and The XDMA module 20 is further configure to read the OCT image data subjected to the image preprocessing from the memory read-write module 30 and send the OCT image data to the upper computer 2 via the PCIE interface 11 to display.

In one embodiment, the image preprocessing module is specifically configured to carry out cubic spline interpolation and Fourier transform on the OCT image data converted into the video timing sequence and send the OCT image data to the VIDEO to AXIS module.

In one embodiment, the image preprocessing module is further specifically configured to transform the OCT image data converted into the video timing sequence into a wavenumber domain before carrying out the cubic spline interpolation and the Fourier transform on the OCT image data converted into the video timing sequence.

Embodiment 3

Figure 3:
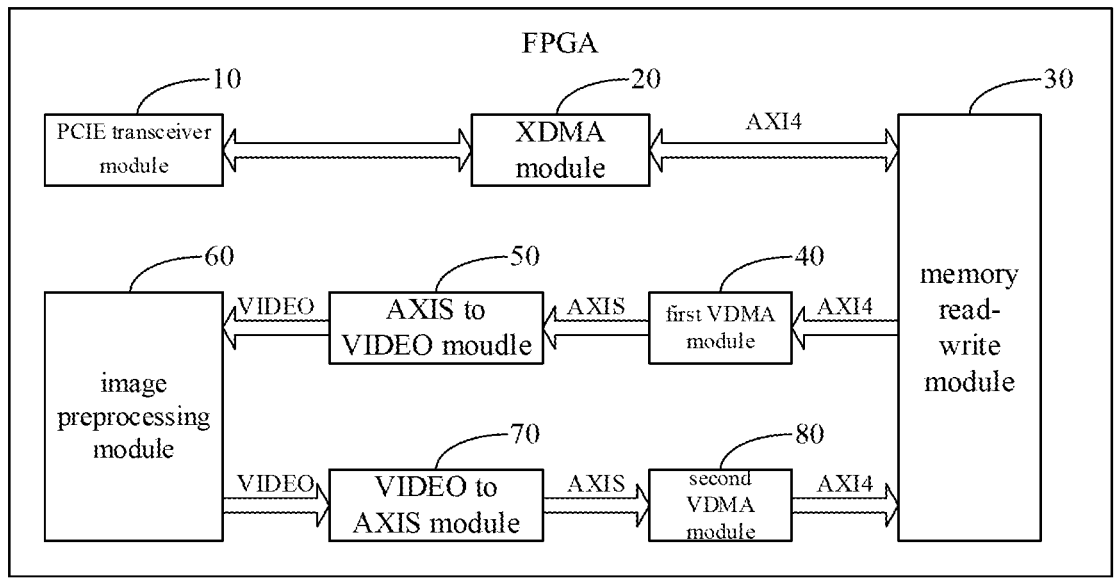
FIG. 3 is a structural view of an FPGA according to Embodiment 3 of the invention.

As shown in FIG. 3, in this embodiment, the XDMA module 20 is in communication connection with the PCIE interface 11 through a PCIE bus and is in communication connection with the memory read-write module 30 through an AXI4 bus.

The XDMA module 20 is specifically configured to write the OCT image data received through the PCIE bus via the PCIE interface 11 into the memory read-write module 30 through the AXI4 bus.

In a specific application, the OCT image data is written into the memory read-write module via the PCIE interface by means of an XDMA IP provided by the XDMA module, and PCIE communication is initiated by the upper computer.

As shown in FIG. 3, in this embodiment, the first VDMA module 40 is in communication connection with the memory read-write module 30 through an AXI4 bus and is in communication connection with the AXIS to VIDEO module 50 through an AXIS bus; and The first VDMA module 40 is specifically configured to read the OCT image data cached in the memory read-write module 30 through the AXI4 bus and send the OCT image data to the AXIS to VIDEO module 50 through the AXIS bus.

In a specific application, the data can be written into a DDR via a write channel of the VDMA, and the data can be read from the DDR via a read channel. The VDMA is essentially the core used for realizing data transfer, thus facilitating the data being written into or read out of the DDR. The first VDMA module is configured to write the data into the DDR.

As shown in FIG. 3, in this embodiment, the VIDEO to AXIS module 70 is in communication connection with the second VDMA module 80 through an AXI4 bus.

The VIDEO to AXIS module 70 is specifically configured to send the OCT image data subjected to the image preprocessing to the second VDMA module 80.

As shown in FIG. 3, in this embodiment, the second VDMA module 80 is in communication connection with the memory read-write module 30 through an AXI4 bus.

The second VDMA module 80 is particularly configured to write the OCT image data subjected to the image preprocessing into the memory read-write module 30 through the AXI4 bus.

In a specific application, the second VDMA module is configured to read the data from the DDR.

Embodiment 4

Figure 4:
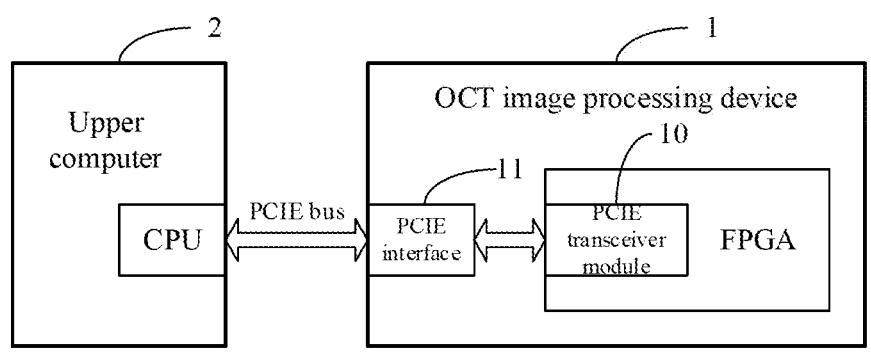
FIG. 4 is a structural view of an OCT image processing system according to Embodiment 4 of the invention.

As shown in FIG. 4, an OCT image processing system 100 comprises the OCT image processing device 1 according to any one of Embodiments 1-3 and the upper computer 2 in communication with the OCT image processing device 1, wherein the upper computer 2 comprises a CPU (Central Processing Unit) which is in communication with the PCIE interface 11 through a PCIE bus.

The upper computer 2 is configured to acquire the OCT image data and send the OCT image data to the PCIE interface 11.

The image preprocessing device 1 is configured to receive the OCT image data via the PCIE interface 11, carry out the image preprocessing on the OCT image data by means of the FPGA, and send, via the PCIE interface, the OCT image data in various stages of the image preprocessing process or the OCT image data after the image preprocessing to the upper computer 2 to display.

In a specific application, the upper computer controls the camera or a detector in communication connection with the upper computer to acquire the OCT image data.

Figure 5:
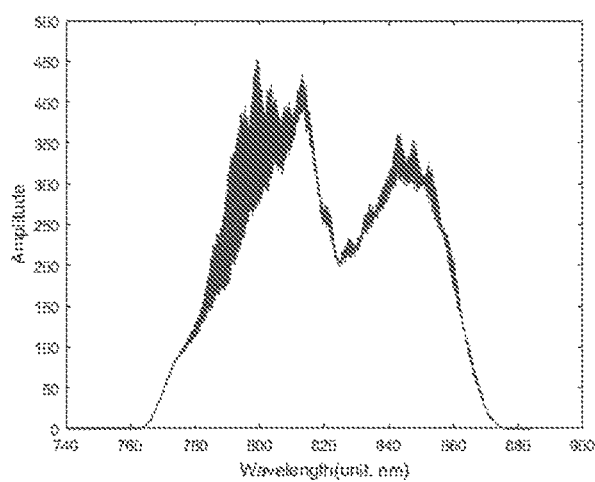
FIG. 5 is a spectrum diagram of OCT image data in a wavelength domain according to Embodiment 4 of the invention.
Figure 6:
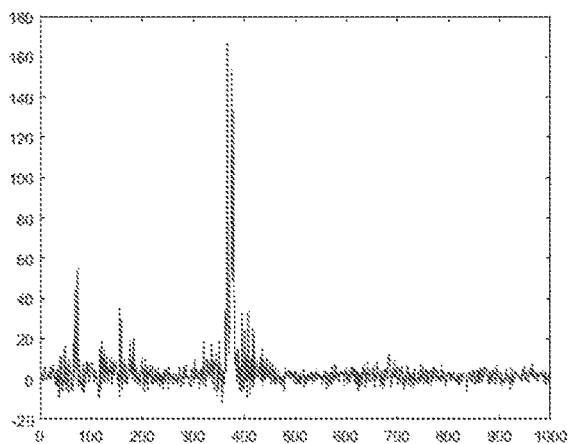
FIG. 6 is a spectrum diagram of OCT image data after being transformed into a wave-number domain and subjected to cubic spline interpolation, according to Embodiment 4 of the invention.
Figure 7:
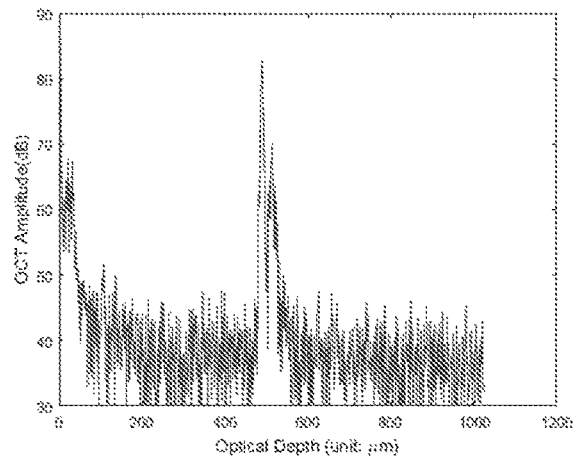
FIG. 7 shows A-SCAN signals obtained after Fourier transform according to Embodiment 4 of the invention.

FIG. 5 illustratively shows a spectrum diagram of the OCT image data in a wavelength domain;

FIG. 6 illustratively shows a spectrum diagram of the OCT image data which is transformed into the wave-number domain and subjected to the cubic spline interpolation;

FIG. 7 illustratively shows A-SCAN signals after the Fourier transform; and

Figure 8:
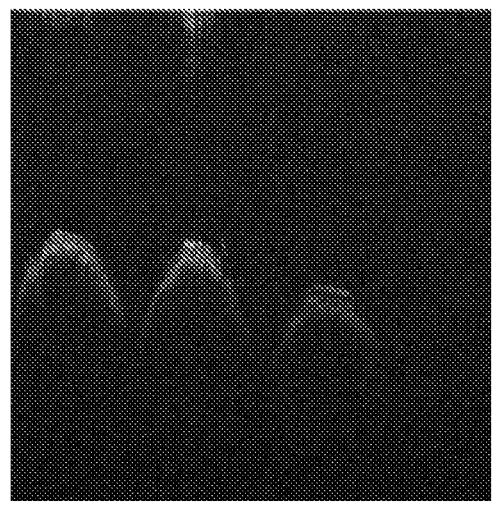
FIG. 8 is a B-SCAN image formed by 1000 A-SCAN signals according to Embodiment 4 of the invention.

FIG. 8 illustratively shows a B-SCAN image formed by 1000 A-SCAN signals.

The embodiments of the present invention provide an OCT image processing device comprising an FPGA. The FPGA is in communication connection with an upper computer via a PCIE interface to receive the OCT image data acquired by the upper computer. The FPGA carries out the image preprocessing on the OCT image data and then send the OCT image data to the upper computer to display. The OCT image data is acquired and displayed by the upper computer and is subjected to the image preprocessing by the FPGA, so that the processing efficiency of the OCT image data is greatly improved.

The above embodiments are only used for explaining the technical solutions of the invention instead of limiting the technical solutions of the invention. Although the invention is detailed with reference to the above embodiments, those ordinarily skilled in the art can still make modifications on the technical solutions recorded in the above embodiments or equivalent replacements on partial technical features of the technical solutions, and all these modifications or replacements should also fall within the protection scope of the invention as long as the essence of the corresponding technical solution does not deviate from the spirit and scope of the technical solutions of the embodiments of the invention.

What is claimed is:

1. An OCT image processing device, comprising an FPGA and a PCIE interface, wherein the FPGA comprises a PCIE transceiver module which is in communication connection with an upper computer via the PCIE interface;

the upper computer is configured to acquire OCT image data and send the OCT image data to the PCIE interface; and the FPGA is configured to receive the OCT image data via the PCIE interface, carry out image preprocessing on the OCT image data, and send, via the PCIE interface, the OCT image data subjected to the image preprocessing to the upper computer to display;

wherein the FPGA comprises an XDMA module, a memory read-write module, a first VDMA module, an AXIS to VIDEO module, an image preprocessing module, a VIDEO to AXIS module, and a second VDMA module, wherein:

the XDMA module is in communication connection with the PCIE interface and the memory read-write module, the memory read-write module is in communication connection with the first VDMA module and the second VDMA module, the first VDMA module is in communication connection with the AXIS to VIDEO module, the AXIS to VIDEO module is in communication connection with the image preprocessing module, the image preprocessing module is in communication connection with the VIDEO to AXIS module, and the VIDEO to AXIS module is in communication connection with the second VDMA module;

the XDMA module is configured to receive the OCT image data sent from the upper computer via the PCIE interface and write the OCT image data into the memory read-write module;

the memory read-write module is configured to cache the OCT image data;

the first VDMA module is configured to read the OCT image data from the memory read-write module and send the OCT image data to the AXIS to VIDEO module;

the AXIS to VIDEO module is configured to convert a timing sequence of the OCT image data into a video timing sequence and send the converted OCT image data to the image preprocessing module;

the image preprocessing module is configured to carry out image preprocessing on the OCT image data converted into the video timing sequence and send the OCT image data subjected to the image preprocessing to the VIDEO to AXIS module;

the VIDEO to AXIS module is configured to send the OCT image data subjected to the image preprocessing to the second VDMA module through an AXI4 bus;

the second VDMA module is configured to write the OCT image data subjected to the image preprocessing into the memory read-write module;

the memory read-write module is further configured to cache the OCT image data subjected to the image preprocessing; and the XDMA module is further configured to read the OCT image data subjected to the image preprocessing from the memory read-write module and send, via the PCIE interface, the OCT image data to the upper computer to display.

2. The OCT image processing device according to claim 1, wherein the XDMA module is in communication connection with the PCIE interface through a PCIE bus and is in communication connection with the memory read-write module through an AXI4 bus; and the XDMA module is specifically configured to write the OCT image data received via the PCIE interface into the memory read-write module through the AXI4 bus.

3. The OCT image processing device according to claim 1, wherein the first VDMA module is in communication connection with the memory read-write module through an AXI4 bus and is in communication connection with the AXIS to VIDEO module through an AXIS bus; and the first VDMA module is specifically configured to read the OCT image data cached in the memory read-write module through the AXI4 bus and send the OCT image data to the AXIS to VIDEO module through the AXIS bus.

4. The OCT image processing device according to claim 1, wherein the image preprocessing module is specifically configured to carry out cubic spline interpolation and Fourier transform on the OCT image data converted into the video timing sequence and send the OCT image data to the VIDEO to AXIS module.

5. The OCT image processing device according to claim 4, wherein the image preprocessing module is further specifically configured to transform the OCT image data converted into the video timing sequence into a wave-number domain before carrying out the cubic spline interpolation and the Fourier transform on the OCT image data converted into the video timing sequence.

6. The OCT image processing device according to claim 1, wherein the VIDEO to AXIS module is in communication connection with the second VDMA module through an AXIS bus; and
    the VIDEO to AXIS module is specifically configured to send the OCT image data subjected to the image preprocessing to the second VDMA module through the AXIS bus.

7. The OCT image processing device according to claim 1, wherein the second VDMA module is in communication connection with the memory read-write module through an AXI4 bus; and
    the second VDMA module is specifically configured to write the OCT image data subjected to the image preprocessing into the memory read-write module through the AXI4 bus.

8. The OCT image processing device according to claim 1, wherein the upper computer comprises a CPU which is in communication connection with the PCIE interface through a PCIE bus.

9. An OCT image processing system, comprising:
    the OCT image processing device according to claim 1; and
    an upper computer in communication connection with the OCT image processing device.

\* \* \* \* \*